US012789006B2

(12) United States Patent
Carstensen et al.

(10) Patent No.: US 12,789,006 B2
(45) Date of Patent: Nov. 10, 2026

(54) PHOTOTHERAPEUTIC APPARATUS

(71) Applicant: Optoceutics ApS, Kongens Lyngby (DK)

(72) Inventors: Marcus Carstensen, Frederiksberg (DK); Ngoc Mai Nguyen, San Jose, CA (US)

(73) Assignee: Optoceutics ApS, Kongens Lyngby (DK)

( * ) Notice: Subject to any disclaimer, the term of this patent is extended or adjusted under 35 U.S.C. 154(b) by 160 days.

(21) Appl. No.: 18/136,875

(22) Filed: Apr. 20, 2023

(65) Prior Publication Data

US 2023/0256262 A1 Aug. 17, 2023

Related U.S. Application Data

(63) Continuation-in-part of application No. 17/507,275, filed on Oct. 21, 2021, now Pat. No. 12,629,539.

(51) Int. Cl.
*A61N 5/06* (2006.01)

(52) U.S. Cl.
CPC .... *A61N 5/0622* (2013.01); *A61N 2005/0652* (2013.01); *A61N 2005/0663* (2013.01)

(58) Field of Classification Search
CPC .......... A61N 5/0622; A61N 2005/0652; A61N 2005/0663; A61N 2005/0626; A61N 2005/0648; A61N 5/0618; A61B 5/163; A61B 5/374; A61B 5/375; A61B 5/378; A61B 5/4836; A61B 5/0077
See application file for complete search history.

(56) References Cited

U.S. PATENT DOCUMENTS 8,576,171 B2 11/2013 Grant
10,279,192 B2 5/2019 Malchano et al.
(Continued)

FOREIGN PATENT DOCUMENTS

JP 2021194356 A * 12/2021
WO WO 2022/056002 3/2022
WO WO 2022/056002 A1 3/2022

OTHER PUBLICATIONS

PCT ISR mailed Jun. 26, 2024.
(Continued)

*Primary Examiner* — Benjamin J Klein
*Assistant Examiner* — Alisha J Sircar
(74) *Attorney, Agent, or Firm* — Patent Law Group; Brian Ogonowsky

(57) ABSTRACT

A phototherapeutic apparatus for emitting therapeutic light, the apparatus comprising: a first set of one or more light sources and a second set of one or more light sources; a control module configured to control the first and second set of light sources; wherein the control circuit is configured to: control the first set of light sources to generate first light, the first light varying periodically at a first brain stimulation rate; control the second set of light sources to generate second light concurrently with the first set of light sources generating the first light, the second light varying periodically at a second brain stimulation rate equal to the first brain stimulation rate plus a third brain stimulation rate, wherein the third brain stimulation rate is selected for stimulating neural oscillations at a beat frequency corresponding to said third brain stimulation rate.

20 Claims, 8 Drawing Sheets

(56) References Cited

U.S. PATENT DOCUMENTS

| | | | | |
|---|---|---|---|---|
| 10,328,276 | B2 | 6/2019 | Williams et al. | |
| 2014/0058483 | A1 * | 2/2014 | Zao | A61N 5/06 607/88 |
| 2020/0269065 | A1 * | 8/2020 | Broeng | A61M 21/00 |
| 2020/0360715 | A1 | 11/2020 | Lim | |
| 2022/0406271 | A1 * | 12/2022 | Chen | H04R 3/00 |
| 2023/0270368 | A1 * | 8/2023 | Kim | A61B 5/38 600/559 |

OTHER PUBLICATIONS

Gamma oscillations in the entorhinal-hippocampal circuit underlying memory and dementia. Tomoaki Nakazono. Neurosci Res. Apr. 2018 ; 129: 40-46.

Safety, Feasibility, and Potential Clinical Efficacy of 40Hz Invisible Spectral Flicker versus Placebo . . . Mikkel Agger. Journal of Alzheimer's Disease (2023).

Sant et al., SSVEP at Single and Beating Frequencies Utilizing Perceptual Insights, thesis Radboud University, Nijmegen, Jun. 29, 2012.

Belluscio et al., Cross-Frequency Phase-Phase Coupling Between Theta and Gamma Oscillations in the Hippocampus, Journal of Neuroscience, Jan. 11, 2012.

* cited by examiner

PHOTOTHERAPEUTIC APPARATUS

CROSS-REFERENCE TO RELATED APPLICATIONS

This is a continuation-in-part of U.S. application Ser. No. 17/507,275, filed on Oct. 21, 2021, entitled Modulation of the Theta-Gamma Neural Code With Controlled Light Therapeutics, by Marcus Carstensen et al., incorporated herein by reference.

TECHNICAL FIELD

The present invention relates to a phototherapeutic apparatus, in particular, a phototherapeutic apparatus for light-induced brain stimulation.

BACKGROUND

The use of light-induced gamma brain stimulation has been suggested for various therapeutic and/or preventive applications and/or cognitive training.

Research has provided evidence in mice that stimulation of gamma brain waves reduces Alzheimer's-related proteins and slows neurodegeneration associated with the disease. Gamma brain waves are electrical charges that help link and process information from all parts of the brain. It is believed that similar advantageous effects occur in humans, and such research is on 15 going.

Healthy brains feature rhythmic patterns, or brain waves, that operate at different frequencies. Gamma brain waves, which oscillate at roughly from 20 to 140 Hz, are associated with higher-order cognitive functions and are known to decrease in the brains of people with Alzheimer's disease and other neurological or psychiatric disorders.

It has been discovered that exposing Alzheimer's mouse models to visible-wavelength LED lights flickering (i.e., strobing) at 40 Hz stimulates gamma waves, which not only reduces levels of beta-amyloid and tau (proteins associated with Alzheimer's) but also boosts the activity of microglia in clearing harmful debris. In other words, such strobing triggers brain wave oscillations around 40 Hz.

WO 2018/152255 discloses a light therapy system (e.g., phototherapy device), such as for treatment of Alzheimer's disease, depression, dementia, short-term memory, or for improved learning, improved athletic performance, or improved cognitive performance. This prior art light system comprises a blue light source that operates at a frequency in the range from 20 to 50 Hz (preferably around 40 Hz), whereby the system enables retinal ganglion cells of a human to be exposed in order to stimulate brain waves (gamma oscillations in the human's brain). This prior art method uses light having different wavelength components to mask the flickering so as to increase the comfort of the user.

Gamma wave stimulation using sound (e.g., clicks played at 40 Hz) in Alzheimer's mouse models has related positive effects.

Using optical or sound gamma stimulation resulted in stimulated mice performing better on memory tasks, including recognizing objects and navigating a water maze to find a hidden platform. Researchers also saw changes in activation responses in microglia and astrocytes (cells involved in clearing debris) and in blood vessels.

Mice exposed to a combination of light and sound gamma stimulation expanded the effects beyond the visual and auditory cortex to the prefrontal cortex, an area of the brain important for planning and completing tasks. Using imaging analysis, the scientists found a unique clustering effect of microglia around amyloid deposits in stimulated mice and reduced amyloid pathology. The effects were short-lived, however, diminishing a week after stimulation.

In a study published in the periodical Neuron, MIT researchers tested the effects of longer-term treatment by exposing mouse models with more advanced Alzheimer's disease to up to six weeks of gamma entrainment by visual stimulation. Results showed stimulation increased gamma brain waves in the visual cortex and higher-order brain areas, including the hippocampus and prefrontal cortex. Continuing stimulation also preserved neuronal and synaptic density in these brain regions, improved performance on memory tasks, and reduced inflammation. Findings point to an overall neuroprotective effect, even in the later stages of neurodegeneration, the researchers reported.

Results of this research add to previous investigations of gamma wave stimulation as a possible treatment for Alzheimer's disease in humans.

40 Hz light stimulation has been shown to not only synchronize with the visual cortex, but also synchronize with the hippocampus and the frontal cortex (measured and validated via implants in humans).

Using a strip of LED lights that flickered at different speeds, the researchers found that a single, hour-long treatment of light flashing at 40 Hz increased gamma waves and reduced beta amyloid levels by half in the visual cortex of mice in the very early stages of Alzheimer's. Within 24 hours, however, amyloid levels returned to normal in this brain region, which processes information from the eyes. When the scientists exposed mice with even higher levels of amyloid buildup to one hour of flickering light per day over seven days, the number of amyloid plaques and levels of free-floating amyloid decreased. The treatment also ramped up the efficiency of microglia, reducing the number of amyloid plaques and free-floating amyloid.

As seen, repeated treatments are required for the gamma brain stimulation, and optimal dosages of the gamma brain stimulation light are being determined.

The brain also produces theta waves in the 4-10 Hz range. Theta waves generate the theta rhythm, a neural oscillation in the brain that underlies various aspects of cognition and behavior, including learning, memory, and spatial navigation in many animals. It can be recorded using various electrophysiological methods, such as electroencephalogram (EEG), recorded either from inside the brain or from electrodes attached to the scalp.

At least two types of theta rhythm have been described. The hippocampal theta rhythm is a strong oscillation that can be observed in the hippocampus and other brain structures in numerous species of mammals including rodents, rabbits, dogs, cats, bats, and marsupials. Cortical theta rhythms are low-frequency components of scalp EEG, usually recorded from humans. Theta rhythms can be quantified using quantitative electroencephalography (qEEG) using freely available toolboxes, such as, EEGLAB or the Neurophysiological Biomarker Toolbox (NBT).

In humans, hippocampal theta rhythm has been observed and linked to memory 20 formation and navigation. In addition to the theta rhythm being important for hippocampal function, it is also important for long-range communication between brain regions.

As with rats, humans exhibit hippocampal theta wave activity during REM sleep. Humans also exhibit predominantly cortical theta wave activity during REM sleep.

Increased sleepiness is associated with decreased alpha wave power and increased theta wave power. Meditation has been shown to increase theta power.

In a recent article in "Neuron", Ole Jensen and John Lisman explain that gamma oscillations (40 Hz) and slower theta oscillations (7 Hz) occur in the same brain regions and interact with each other, a process known as cross-frequency coupling. Jensen and Lisman propose that this cross-frequency coupling allows the brain to represent (or code) multiple pieces of information in an ordered way, and cross-frequency coupling can be used to measure the relationship between the phase of the theta oscillations and the envelope of the gamma power. Thus, high values of coupling indicate that gamma amplitude is a strong function of theta phase, see e.g. https://www.ncbi.nlm.nih.gov/pmc/articles/PMC3648857/.

Recent work suggests that this coding scheme coordinates communication between brain regions and is involved in sensory as well as memory processes.

As seen, it is believed that there are significant benefits to human mental and physical health if theta waves and gamma waves, produced in the brain, are sufficiently strong and occur at an optimal phase.

One problem with optically stimulating the brain with gamma and theta waves is that the light flicker at the theta frequency of 4-10 Hz would be extremely uncomfortable to the user over an extended time and may lead to other neurological issues. However, the flicker of the gamma light frequency of 40 Hz is barely perceptible to humans.

It remains desirable to provide an improved phototherapeutic apparatus that is versatile in use, inexpensive in manufacture, and that facilitates exposure of users over an extended period of time in a user-friendly manner.

SUMMARY

According to one aspect, disclosed herein are embodiments of a phototherapeutic apparatus for emitting therapeutic light. Embodiments of the apparatus comprise: a first set of one or more light sources and a second set of one or more light sources; a control module configured to control the first and second set of light sources; wherein the control circuit is configured to:

- control the first set of light sources to generate first light, the first light varying periodically at a first brain stimulation rate;
- control the second set of light sources to generate second light concurrently with the first set of light sources generating the first light, the second light varying periodically at a second brain stimulation rate equal to the first brain stimulation rate plus a third brain stimulation rate, wherein the third brain stimulation rate is selected for stimulating neural oscillations at a beat frequency corresponding to said third brain stimulation rate.

Stimulating neural oscillations at a beat frequency corresponding to a difference between brain stimulation rates of periodically varying light emitted by respective light sources allows stimulation of neural oscillations at many frequencies, including but not limited to frequencies below a critical flicker frequency, without uncomfortable perceptible flicker of the emitted periodically varying light.

Employing respective sets of light sources to generate the first and second light allows for a simple control of the apparatus and allows the emitted light to have a constant and homogenous visual appearance, e.g. without uncomfortable temporal variations in intensity or color.

Preferably the apparatus is configured to generate the periodically varying first and second light such that the periodic variation is substantially imperceptible by the human observer. To this end, in some embodiments, the second brain stimulation rate is higher than a critical flicker frequency (CFF) threshold, and wherein the control module is configured to control the second set of one or more light sources to emit the second light at a varying intensity, varying at the second brain stimulation brain rate. In some embodiments, also the first brain stimulation rate is higher than the critical flicker frequency (CFF) threshold, and the control module is configured to control the first set of one or more light sources to emit the first light at a varying intensity, varying at the first brain stimulation brain rate.

Alternatively, in another embodiment, instead of the light alternating between white and darkness, the light can alternate between two different colors at the respective stimulation frequencies. For example, one light source can alternate at 47 Hz between the color XX and the color YY, and the other light source can alternate at 40 Hz between color ZZ and KK. This is referred to as heterochromatic flicker. The heterochromatic flicker can be constructed by multiple combinations of waveforms.

Such heterochromatic flicker reduces any noticeable flicker yet produces good results. If the two colors are of equal luminance (but still different hues), the flicker should be imperceptible.

Accordingly, in some embodiments, the first brain stimulation rate or both the first and second brain stimulation rates may be smaller than the critical flicker frequency. In such or other embodiments, the control module may be configured to control the first set of light sources to alternatingly generate first and second colored light, alternatingly at said first brain stimulation rate, the first colored light having a first set of color components and the second colored light having a second set of color components different from the first set of color components; wherein the first and second color components are selected such that the alternatingly generated first and second colored light is perceivable by a human observer as light having a user-perceptible first fused color, such as white or another suitable color. Similarly, the control module may be configured to control the second set of light sources to alternatingly generated third and fourth colored light, alternatingly at said second brain stimulation rate, the third colored light having a third set of color components and the fourth colored light having a fourth set of color components different from the third set of color components; wherein the third and fourth color components are selected such that the alternatingly generated third and fourth colored light is perceivable by a human observer as light having a user-perceptible second fused color, such as white or another suitable color. Preferably, the first and second fused color may be selected such that they are perceived as substantially the same color.

Utilizing the non-linearity, especially two-wave, three-wave, or four-wave mixing properties of the brain, other combinations of frequencies can also be generated to stimulate specific dual combinations of frequencies for multiple frequency stimulation of the Theta Gamma coupling.

In another embodiment, the light variation is sinusoidal, and the current to the LEDs is modulated at the first brain stimulation rate (e.g. 40 Hz) and the second brain stimulation rate (e.g. 47 Hz), respectively. This results in stimulation of the brain at both the first frequency (e.g. the gamma frequency of e.g. 40 Hz) and the beat frequency corresponding to the third brain stimulation rate (e.g. a theta frequency of e.g. 7 Hz).

The third brain stimulation frequency may be selected for stimulating neural oscillations in a frequency band of neural oscillations, such as in an alpha, beta, gamma, theta or delta frequency band. Additionally, the first and/or the second brain stimulation frequency may be selected for stimulating neural oscillations in a frequency band of neural oscillations, such as in an alpha, beta, gamma, theta or delta frequency band. The neural oscillations stimulated by the first and/or second brain stimulation rate may be in the same frequency band as the neural oscillations stimulated by the third brain stimulation rate, or in a different frequency band than the neural oscillations stimulated by the third brain stimulation rate.

In some embodiments, the first brain stimulation rate is configured to stimulate neural oscillations at a predetermined brain wave frequency band, in particular in the gamma frequency band, such as between 20 Hz and 140 Hz, preferably between 20 Hz and 60 Hz, such as between 35 Hz and 45 Hz, e.g. 39 Hz or 40 Hz, or between 45 Hz and 140 Hz, such as between 45 Hz and 70 Hz, such as between 45 Hz and 55 Hz, such as at 50 Hz.

In some embodiments, the third brain stimulation rate, i.e. a difference between the second brain stimulation rate and the first brain stimulation rate is between 1 Hz and 140 Hz. In some embodiments, such as between 1 Hz and 12 Hz, such as between 4 Hz and 12 Hz, such as between 4 Hz and 8 Hz, or between 20 Hz and 140 Hz, such as between 20 Hz and 60 Hz, such as between 35 Hz and 45 Hz.

In embodiments for stimulating gamma-theta coupling, a first brain stimulation rate range in a gamma range between 20 Hz-140 Hz may be effective, and a third brain stimulation rate range in a theta range between 4 Hz-10 Hz may be effective. Therefore, the two light flickering frequencies would differ by 4-10 Hz and be in the range of 20-150 Hz.

As mentioned above the periodically varying light may be pulsed light or sinusoidally modulated light. For a pulsed system, a duty cycle of 50% is sufficient, but the duty cycle is not critical. In another embodiment, the varying LED light may be substantially sinusoidal. This may be done by simply smoothing out the pulses with a low pass filter.

In some embodiment, light (optical stimulation), skin stimulation, and audio stimulation, or any combination thereof, may occur simultaneously to stimulate various parts of the brain. In some embodiments, the power source that pulses the LEDs, or creates a sinusoidal light output, may further energize electrodes adhered to the user's skin to provide electric or vibrational stimulation, or may energize a sound system to provide audio stimulation. Any type of sense stimulation will have an effect on the brain to produce or amplify gamma and theta waves in the brain.

Theta-gamma coupling supports memory processes in the entorhinal-hippocampal network. Lower frequency gamma modulated by theta gamma may promote memory retrieval, while higher frequency gamma modulated by theta may facilitate memory encoding.

In some embodiments, the apparatus provides stimulation of the neuronal theta-gamma coupling inside the user's brain using flickering light for therapeutic and diagnostic purposes, such as treatment of Alzheimer's disease or treatment of other neurological and psychiatric disorders (i.e., brain network dysfunctions).

In some embodiments, the apparatus may be used for treating or preventing a neurodegenerative disease, such as Alzheimer's disease, Mild Cognitive Impairment, Multiple Sclerosis, Parkinson's. In some embodiments, the apparatus may be used for treating or preventing a psychiatric disorder, such as depression, major depressive disorder or general anxiety disorder. In some embodiments the apparatus may be used for improving a subject's general wellness, e.g. so as to facilitate healthy aging.

Theta-gamma coupling (TGC) is a form of cross-frequency coupling inside the brain, whereby "high-frequency" gamma (e.g., 30-50 Hz) oscillations are modulated by low-frequency theta (e.g., 4-10 Hz) oscillations.

Accordingly, In some embodiments, a user-operated optical (or photonic) brain stimulation system is disclosed that flickers one or more light sources, such as white light or blue light LEDs, at a particular first brain stimulation rate, e.g. a gamma frequency such as at a rate of 40 Hz, and also flickers one or more white light or blue light LEDs at a second brain stimulation rate, e.g. of 47 Hz., which creates a beat frequency (or subtraction frequency), e.g. of 7 Hz (a theta frequency), inside the brain as well as a gamma frequency of 40 Hz. Thus, induced theta-gamma coupling is created in the brain with little to no experience of perceptible flicker. Since there is no light flickering at the theta frequency, any flickering may be made substantially imperceptible and not annoying. In some embodiments, flickering may be made substantially imperceptible at frequencies above about 30 Hz or 35 Hz, when the flickering is suitably masked, e.g. using Invisible Spectral Flicker (ISF), for example as described in Mikkel Pejstrup Agger et al., "Safety, Feasibility, and Potential Clinical
Efficacy of 40 Hz Invisible Spectral Flicker versus Placebo in Patients with Mild-to-Moderate Alzheimer's Disease: A Randomized, Placebo-Controlled, Double-Blinded, Pilot Study", Journal of Alzheimer's Disease, 92(2), 653-665. https://doi.org/10.3233/JAD-221238.

Other embodiments use a first brain stimulation rate at a gamma frequency, e.g. 40 Hz or 50 Hz, and a second brain stimulation rate, e.g. 80 Hz or 90 Hz, which creates a beat frequency in the gamma frequency range, e.g. a beat frequency of 40 Hz. Since there is no light flickering at a frequency below the first stimulation rate, which may be chosen to be at least 50 Hz, e.g. between 50 Hz and 60 Hz, such as between 50 Hz and 55 Hz, any flickering may be kept substantially imperceptible and not annoying, in some embodiments even without use of masking techniques such as ISF. While ISF or another suitable masking technique may still be useful, stroboscopic flickering at frequencies of 50 Hz or higher are by many subjects not perceived as annoying.

In some embodiments, the third brain stimulation rate is substantially equal to the first brain stimulation rate, such as between 20 Hz and 60 Hz, such as between 35 Hz and 45 Hz, or the third brain stimulation rate and the first brain stimulation rate lie within the same frequency band, such as in the gamma frequency band. For example, first brain stimulation rate may be selected to be between 40 Hz and 60 Hz, such as between 45 Hz and 55 Hz, preferably between 50 Hz and 60 Hz. The third brain stimulation rate may be selected to be between 35 Hz and 45 Hz. Accordingly, the first brain stimulation rate results in a flicker that is perceivable to a lesser degree, if at all, for most subjects, while being in a frequency range at which parvalbumin-positive (PV+) cells have been found to exhibit high local field potentials during optogenetic stimulation (see e.g. Jorge J. Palop and Lennart Mucke, "Network abnormalities and interneuron dysfunction in Alzheimer disease", Nature Reviews, Neuroscience, Vol. 17, December 2016, p 777-792). To this end a first brain stimulation rate at about 50 Hz or slightly larger, e.g. between 50 Hz and 55 Hz is preferred. At the same time, the third brain stimulation rate of about 40 Hz also lies in the frequency range at PV+ cells have been found to exhibit high local field potentials during optogenetic stimulation and a frequency which has been found to reduce beta amyloid levels by half in the visual cortex of mice in the very early stages of Alzheimer's. Generally, it may be desirable to increase, preferably maximize, stimulation of PV+ cells.

In some embodiments the first brain stimulation rate or the third brain stimulation rate is chosen to correspond to a frequency of electrical oscillations generated in bundles of brain microtubules, in particular frequencies between 38 Hz and 40 Hz, such as about 39 Hz. Microtubules are long cylindrical structures of the cytoskeleton that control cell division, vesicular transport, and the shape of cells. Microtubules are highly charged and behave as nonlinear electrical transmission lines. Recent studies have determined that bundles of brain microtubules are electrically active, generating electrical oscillations in the 39 Hz range that correlate well with oscillatory activity observed in neurons and brain function, see e.g. María del Rocío Cantero and Horacio F. Cantiello, "Microtubule Electrical Oscillations and Hippocampal Function", J Neurol Neuromedicine (2020) 5(3): 1-5.

In some embodiments, one or both of the first and second generated light is white light or light that is perceivable by a human observer as white light, which has been found to provide a low degree of discomfort even during extended exposure. In some embodiments, the color and/or brightness of the first and/or second light is user-adjustable, thereby allowing a user to adjust the light so as to obtain a high degree of comfort.

In some embodiments, the first and second light have substantially the same perceivable color and/or the same perceivable brightness, thereby providing a low degree of discomfort even during extended exposure. To this end, the luminous emittance of the first and second set of light sources may be substantially uniform. In some embodiments the apparatus comprises at least one light-emitting member, such as at least one screen, at least one panel or the like. The at least one light-emitting member defines at least one light emitting surface from which light is emitted. The at least one light emitting surface may be a planar surface or a curved surface. The light-emitting member may be a diffuser or otherwise be configured to produce diffused light. The at least one light emitting surface defines a first surface portion and a second surface portion, different and, preferably separate, from the first surface portion. The apparatus is configured to emit the first light from said first surface portion, in particular only from said first surface portion, and the second light from said second surface portion, in particular only from said second surface portion. While the first and second surface portions may overlap, in some embodiments, it may be preferred that any overlapping portion is only a minor part of the first and second surface portions, such as less than 40%, preferably less than 30%, such as less than 20%, such as less than 10% of the first and/or second surface portion. In some embodiments, the first and second surface portions are completely separate, i.e. they do not overlap. The first and second surface portions may be adjacent to each other, e.g. directly adjacent from each other or spaced apart from each other. For example, the first and second surface portions may be arranged side by side, e.g. formed as respective halves of a light-emitting screen or panel. Preferably, the first and second surface portions are arranged horizontally next to each other when the apparatus is in its intended operational position. While the first and second surface portions may have shapes and/or sizes different from each other, it may be preferred that the first and second surface portions have the same size and/or shape so as to provide a uniform stimulation by the first and second light. The first and second surface portions may each be extended surfaces having a surface area of at least 10 $cm^2$, such as at least 20 $cm^2$, such as at least 50 $cm^2$, such as at least 100 $cm^2$, such as at least 200 $cm^2$. It will be appreciated, however, that embodiments with even considerably larger surface areas may be used, e.g. surface areas of up to 500 $cm^2$, such as up to 1 $m^2$, or even larger. The extended surface area of the first surface portion may be defined by a single shape, i.e. by a single, closed boundary. Similarly, the extended surface area of the second surface portion may be defined by a single shape, i.e. by a single, closed boundary.

In some embodiments, each of the first and second surface portion has between 30% and 70% of the surface area of the light-emitting surface, such that the first and second surface portions together have between 80% and 100% of the light emitting surface area.

For example, the first and second sets of light sources and the light emitting member may form a display screen of an electronic device, such as a tablet, a laptop computer, a TV screen, or the like. The first and second surface portions may be formed as a left and right portion, in particular a left and right halve, respectively of the display area of the display area of the display screen.

In other embodiments, the light emitting member may be formed as a, preferably planar, panel. The first and second surface portions may be formed as respective portions, in particular respective halves of the light emitting panel, such as left and right portions, in particular a left and right halves, respectively of the light emitting panel. The light emitting panel may be a diffuser panel which may be formed as part of a housing of the apparatus. The diffuser panel defines an outwardly directed light-emitting surface configured to be viewed by a user of the apparatus and an inwardly directed surface, opposite the outwardly directed surface. The first set of light sources may be configured to direct the first light to a first surface portion of the inwardly directed surface of the diffuser panel so as to cause the first light to be emitted as first diffused light by a corresponding first surface portion of the outwardly directed surface of the diffuser panel. Similarly, the second set of light sources may be configured to direct the second light to a second surface portion of the inwardly directed surface of the diffuser panel so as to cause the second light to be emitted as second diffused light by a corresponding second surface portion of the outwardly directed surface of the diffuser panel. The apparatus may include an internal reflector, baffle or other divider configured to prevent light from the first set of light sources to be emitted via the second surface portion, and to prevent light from the second set of light sources to be emitted via the first surface portion. Accordingly, the apparatus may be embodied as a luminaire comprising a housing, the first and second sets of light sources, and the control circuit.

Accordingly, in some embodiments, the phototherapeutic apparatus comprises a housing configured to accommodate the first and second sets of light sources; the housing defining a light-output panel, in particular a diffuser panel, for outputting the first and second light towards a user; wherein the light-output panel defines a first surface portion and a second surface portion, different from the first surface portion; wherein the apparatus is configured to output the first light at least predominantly through the first surface portion and to output the second light at least predominantly through the second surface portion.

Preferably, the apparatus is configured to emit the first light from the first surface portion with a uniform first luminous emittance across the first surface portion, and to emit the second light from the second surface portion with a uniform second luminous emittance across the second surface portion, preferably substantially equal to the first luminous emittance. Preferably the first and second luminous emittances are sufficiently uniform to be perceived by a human observer as providing a light emitting surface of substantially uniform brightness or at least without distracting or even annoying variations in brightness.

While other types of light sources may be used, in some embodiments, the first set of light sources comprises a first set of light emitting diodes (LEDs), and the second set of light sources comprises a second set of light emitting diodes (LEDs).

While the light source output power should be at a comfortable level for the person, such as a patient or any other person looking at it, a precise output power does not seem critical. The optimal dosage may be preprogrammed into the system. An optimal dosage for the particular person, such as a patient, may be, for example, one continuous hour every day for example at 9 am. By precisely monitoring dosages for many similar persons and storing the information, while also testing the persons for changes in the disease, a correlation can then be developed between dosage and patient improvement.

Various areas of the brain can be stimulated by optical brain stimulation treatment such as the hippocampus, amygdala, prefrontal cortex (PFC), visual cortex (VC), and the suprachiasmatic nucleus (SCN). The ability to determine the optimal target effective dosage of optical brain stimulation for these particular areas of the brain will aid in the treatment of diseases that are associated with neurodegeneration. In particular, understanding the minimal dosage required to activate the hippocampus and SCN to affect circadian rhythm (often associated with early onset of Alzheimer's) may allow for individualize/personalize treatment of diseases.

One can examine dose dependence of activation of cytokines within 15 minutes of light exposure, while it takes 60 minutes to activate autoimmune cells. So, knowing when certain enzyme and transcription/translation activation occurs may be useful for determining the required treatment duration (or dosage), and the treatment can be personalized to each person.

In some embodiments, the apparatus comprises one or more EEG sensors for detecting brain waves; and a processing system coupled to detect first signals corresponding to the brain waves and coupled to control one or more attributes of the generated light from the light source to increase one or more predetermined neural oscillation, such as to increase theta-gamma wave coupling in the person's brain. The one or more attributes may be chosen to include one or more attributes selected from: the luminous emittance, a modulation depth of the periodically varying first and/or second light, the first, second and/or third brain stimulation rate, a relative phase between the periodically varying first and second light, a session duration. Accordingly, the light emission may adaptively be adjusted to a particular user so as to increase the desired effect of the light therapy for the particular user.

In some embodiments, the one or more EEG sensors is configured to detect electrical emissions from at least one of the MEC and hippocampus areas of the person's brain.

In some embodiments, the phases of the gamma and theta waves in the brain, as a result of the stimulation, are measured in real-time by, for example, detecting EEG (electroencephalogram) signals, using implants, or using other methods for measurement of brain activity. Then the phase of the light stimulus is controlled (by shifting the stimulus pulses in time) so that the brain is stimulated at a certain phase to ensure optimal neuronal theta-gamma coupling through a phase feedback mechanism. The active measurement of phase during treatment, and then the use of the EEG feedback to dynamically adjust the stimulus, results in the stimulus being phase-locked to either a natural theta rhythm (the one that is there always) or to an induced theta rhythm (the brain rhythm that is stimulated by light, sound, haptic, electrical/magnetic stimulation. etc.).

To provide a more accurate determination of the effective dosage, some embodiments of the apparatus may comprise an eye tracking system that is configured to detect the person's gaze angle relative to the light source during the stimulation session.

Accordingly, the phototherapeutic apparatus may comprise:

a processing system;

an eye-tracking device that detects said person's eye and provides first data to the processing system, wherein the processing system is configured to use the first data to adjust aspects of a brain stimulation session.

In particular, the first data is indicative of at least the person's gaze angle with respect to the first and/or second sets of light sources A maximum dosage is delivered when the person is directly looking at the light source at a particular distance (e.g., 50 cm). In that case, the dosage time can be the minimum. If the person looks away from the light source for periods of time during the treatment, the non-zero gaze angle is processed using an algorithm to extend the dosage time, so the person receives the overall correct dosage for the day.

The gaze tracker can also determine the distance the eye is from the light source and the diameter of the pupil. These factors also affect the effective dosage, and the system dynamically controls the dosage time or even the light output power to compensate for eye distance and pupil size.

The apparatus may further comprise a display of a duration of the brain stimulation session as the session is adjusted. A display may tell the person the remaining time for the treatment, which dynamically adjusts for the person's gaze. Therefore, the person is encouraged to gaze directly at the light source to minimize the session time.

The system may be incorporated into a desk-supported system, portable screens and tablets, smart phones, flat or curved screens, wearable goggles, or other types of flat, curved, round or otherwise differently shaped optical screen or light-source systems.

The processing system may be configured to adjust a duration of the brain stimulation session based on the first data. In one embodiment, the processing system is configured to extend the duration of the brain stimulation session based on the first data.

The eye-tracking device may comprises a camera.

The processing system may be configured to receive a target dosage of the brain stimulation, corresponding to a brain stimulation session time, and the first data may be used to adjust a duration of the session time.

The apparatus may further comprise a memory, wherein second data corresponding to the brain stimulation session is stored in the memory for later retrieval.

In some embodiments, the apparatus further comprises a communications system, wherein the communications system transmits second data relating to the session for use in determining an efficacy of the brain stimulation.

According to one aspect, disclosed herein is a method to stimulate the neuronal theta-gamma coupling or other neural oscillation activity inside the brain using flickering light for therapeutic and diagnostic purposes, such as treatment of Alzheimer's disease or treatment of other neurological and psychiatric disorders (i.e., brain network dysfunctions). Theta-gamma coupling (TGC) is a form of cross-frequency coupling inside the brain, whereby "high-frequency" gamma (e.g., 30-50 Hz) oscillations are modulated by low-frequency theta (e.g., 4-10 Hz) oscillations. The method may use an embodiment of the apparatus disclosed herein.

BRIEF DESCRIPTION OF THE DRAWINGS

Elements labelled with the same numerals in the various drawings may be the same or equivalent.

DETAILED DESCRIPTION

Figure 1:
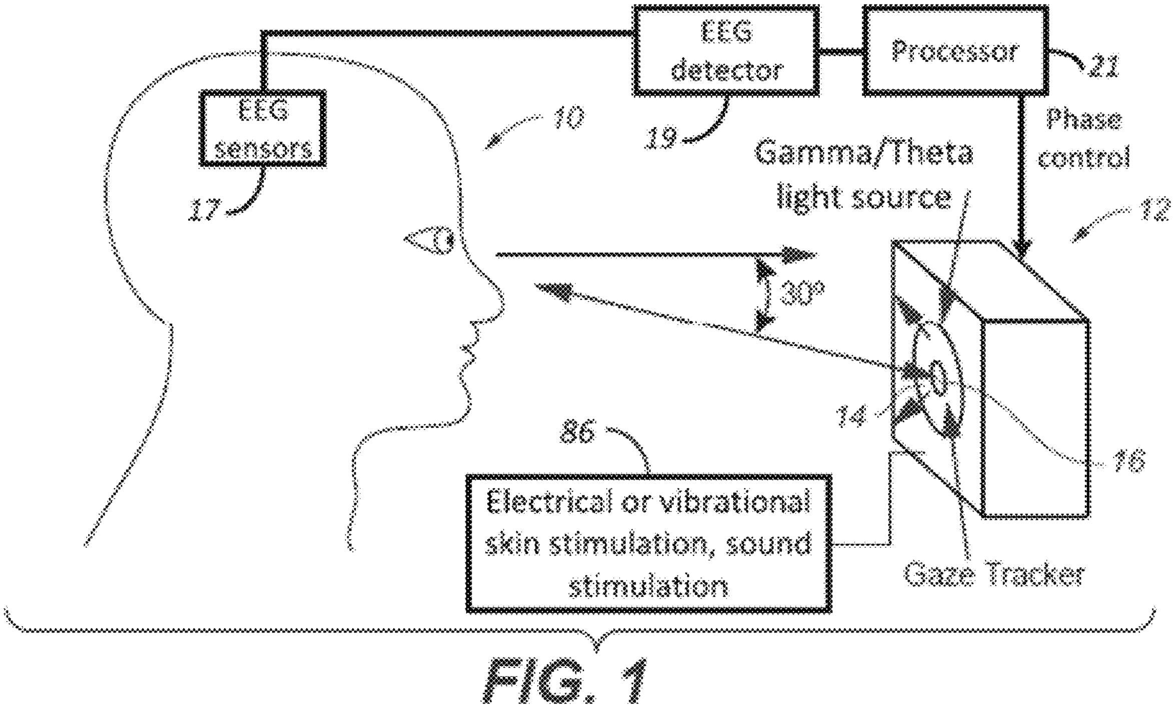
FIG. 1 illustrates the optical gamma/theta brain stimulator with a dosage adjuster, in accordance with one embodiment of the invention.

FIG. 1 illustrates a subject, such as a person 10, that either has been diagnosed with Alzheimer's disease or may be at risk of developing Alzheimer's or other brain disease, or diagnosed with a circadian rhythm sleeping disorder, where the disease or disorder may be treated with optical, modulated gamma/theta brain stimulation. The person 10 may additionally be subjected to or treated with skin or sound gamma/theta brain stimulation.

A gamma/theta brain stimulation light system 12 is positioned about 50-100 cm from the person 10. The system may be supported by a table or desk. In another embodiment, the system 5 forms goggles that are worn by the person 10. In one embodiment, the system uses an apparatus as described in connection with FIG. 7 below.

In one embodiment, a pulsing light source 14 uses blue light LEDs, white light LEDs, or a variety of different wavelength monochromatic LEDs.

One set of LEDs is energized at 40 Hz (or other first brain stimulation rate e.g. anothr gamma frequency) and another set of LEDs is simultaneously energized at 47 Hz (or other second brain stimulation rate). The combined light 10 perceived by the person's brain will be 40 Hz and a beat frequency (subtraction frequency) of 7 Hz (or another third brain stimulation rate, e.g. another theta frequency or a gamma frequency. The flickering is near to imperceptible at 40 Hz.

The 40 Hz and 47 Hz frequencies are preferred in one embodiment when gamma-theta coupling is intended, but not required. A gamma brain stimulation rate range between 20 Hz-140 Hz may be effective, and a theta brain stimulation rate range between 4 Hz-10 Hz may be effective. Therefore, the two light flickering frequencies may differ by 4-10 Hz and be in the range of 20-150 Hz. This would result in the brain being stimulated at the gamma frequency and the beta theta frequency.

In embodiments, where only gamma stimulation is intended, the two light flickering frequencies may differ by 20-150 Hz, such as by between 35 Hz and 50 Hz and be in the range of 20-150 Hz, such as between 35 Hz and 55 Hz.

In one embodiment, the LEDs are optionally arranged to form a circular light source 14 with a camera lens 16 in the middle. In another embodiment, the light source 14 may be more of a point source, and the camera lens 16 may be next to it. In yet another embodiment, the light source is an extended surface, such as a rectangular surface, and the camera lens 16 may be next to it of embedded in the center of the surface. When the camera is located next to the surface, the gaze angle is adjusted for the offset of the lens and the light source. The light source 14 may instead be a flat two-dimensional array of LEDs, such as 20 cm×20 cm diffused Lambertian source.

In another embodiment, the LEDs are energized to output light whose amplitude is sinusoidal. In such a case, the energizing currents to different sets of LEDs are 40 Hz and 47 Hz, so there is no perceived flicker.

In another embodiment, the LEDs are energized for a time (a few seconds) at 40 Hz, followed by being energized for a few seconds at 47 Hz, where the alternation is less than 6 seconds. The brain will perceive the frequencies as being modulated.

In another embodiment, instead of the light alternating between white and darkness, the light can alternate between different colors at the stimulation frequencies, such as between green and red and between blue and yellow. For example, one light source can alternate at 47 Hz between the colors XX and the color YY, and the other light source can alternate at 40 Hz between the colors ZZ and KK. This is referred to as heterochromatic flicker or Invisible Spectral Flicker (ISF), e.g. as described in M. P. Agger et al. "Novel Invisible Spectral Flicker Induces 40 Hz Neural Entrainment with Similar Spatial Distribution as 40 Hz Stroboscopic Light", J Alzheimers Dis. 2022; 88(1): 335-344 or as described in Mikkel Pejstrup Agger et al., "Safety, Feasibility, and Potential Clinical Efficacy of 40 Hz Invisible Spectral Flicker versus Placebo in Patients with Mild-to-Moderate Alzheimer's Disease: A Randomized, Placebo-Controlled, Double-Blinded, Pilot Study", Journal of Alzheimer's Disease, 92(2), 653-665. https://doi.org/10.3233/JAD-221238. The heterochromatic flicker can be constructed by multiple combinations of waveforms. Such heterochromatic flicker reduces any noticeable flicker yet produces good results. If the colors are of equal luminance (but still different hues), the flicker should be imperceptible.

The overall dosage of light for the person 10 may be determined by a medical worker based on clinical trials and testing. Optimal dosage levels for different types of persons, such as patients, are still being studied, but a reasonable dosage is one-hour of the person 10 looking directly at the light source 14. Such a session may be performed at the same time every day. The person 10 may be periodically evaluated by a medical worker to correlate the gamma brain stimulation with the effects of Alzheimer's or other disorder. Cognitive testing may be done as 15 well as testing to determine the presence of certain proteins and other chemicals in the person's body. Testing may include an EEG (electroencephalography). It is vital, for evaluation, to know exactly what dosage of light has been given to the person 10.

The Applicants have discovered that the effective dosage of neural entrainment light is highly influenced by combinations of gaze angle, eye distance from the light source, and pupil 20 size, although compensation for any one of these factors helps achieve the target dosage. When the apparatus emits light from different light emitting surface portions, e.g. in a side-by-side arrangement, the gaze angle is a particularly important parameter. The actual dosage corresponds to a certain brain stimulation session duration given the particular gaze angles, eye distances, and/or pupil sizes during the session. Adjustments for gaze angle are the most significant for achieving the target light dosage.

The camera 18 (FIG. 2) and lens 16 may be of a conventional type used for gaze tracking. Conventional software and processing hardware may also be used to detect the gaze angle, eye/face distance, and pupil size. The camera 18 may emit infrared signals and detect the reflection in order to determine the gaze angle, eye/face distance, and pupil size. Alternatively, the camera 18 may use image processing to calculate gaze angle, eye/face distance, and pupil size. Calibration by the person may be initially used to establish baselines, where the person 10 is instructed to look at different areas at different distances to establish the baseline data. That baseline data is then stored in a memory for later comparison to the data collected during a session.

A target light dosage is first established by the medical worker for the person 10 and this information is downloaded into the system 12, such as through the Internet. The target light dosage correlates to the session duration, given a known light optical output power and pulse frequency, with the person at a particular distance from the light source with an average pupil size. In one example, this target dosage assumes the person 10 is directly looking at the light source 14 at a distance of 50 cm with an average pupil size. The actual effective dosage, 10 however, is reduced if the person 10 does not look directly at the light source 14, or is further than 50 cm away, or has a smaller than average pupil size.

As described with respect to FIGS. 2-5, the gaze angle, eye distance from the light source, and pupil size are automatically detected by the camera and algorithms, and the session duration is expanded as necessary to achieve the predetermined target light dosage. For example, a gaze angle of 0° is looking directly at the light source 14, so the person 10 receives 100% of the dosage at 50 cm with average pupil size. A gaze angle of 90° results in the person 10 receiving 0% of the light, and a gaze angle of 45° results in the person 10 receiving 50% of the light. The correlation between detected gaze angle and light reception may be linearly extrapolated between 0-100%, or the correlation may be non-linear based on empirical results.

The detected distance from the light source will have a non-linear correlation to the actual effective dosage since the effect of the light is non-linearly diminished as the person 10 moves from 50 cm to 100 cm from the light source. Similarly, the pupil size has a non-linear effect on the actual dosage.

Also, as shown in FIG. 1, an EEG feedback system may be used to dynamically optimize the phase of the stimulation pulses to maximize coupling between the brain's gamma rhythms and theta rhythms. Recent evidence suggests that good memory performance requires coupling, within the brain, gamma rhythms (about 30-140 Hz) to particular phases of the theta cycle. The theta-gamma coupling is thought to facilitate transfer of information throughout the entorhinal hippocampal network. Activating gamma-modulated cell assemblies at a particular theta phase may allow the network to produce a more powerful output by ensuring that distributed cells fire closely in time. Such a mechanism may serve to facilitate either memory encoding or memory retrieval, depending on which type of gamma rhythms are recruited.

An EEG is normally used as a test that detects abnormalities in brain waves or abnormalities in the electrical activity of the brain. During the procedure, electrodes consisting of small metal discs with thin wires are pasted onto the user's scalp or positioned close to the scalp such as by using a headpiece. The electrodes detect weak electrical emissions that result from the activity of the brain cells.

Some embodiments of the present apparatus instead detect the EEG signals from the brain to detect the coupling of the gamma and theta rhythms and then adjust the phase of the light stimulation pulses to maximize the coupling.

Figure 6:
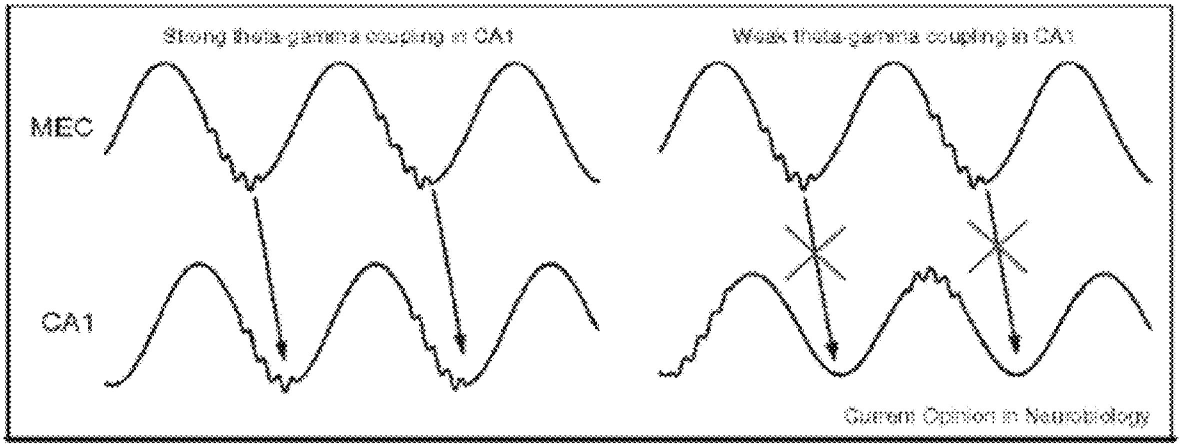
FIG. 6 illustrates the desired theta-gamma wave coupling in the brain.

In FIG. 1, conventional sensors 17, such as metal electrodes, are placed on or near the person's scalp. The EEG signals are sensed using a conventional EEG detector 19. The sensors 17 are placed to sense signals from the medial entorhinal cortex (MEC) and the CA1 region of the hippocampus. The correct placement of such sensors 17 would be known to those skilled in the art. The conventional EEG detector 19 then reads the two brain waves. A processor 21 then detects the two waves and adjusts the phase of the light stimulation pulses so the two detected waves have the maximum coupling. This is shown in FIG. 6 where the detected MEC and CA1 waveforms on the left show a desirably strong theta-gamma coupling, due to the proper phase adjustment by the processor 21, and the waveforms on the right show a weak theta-gamma coupling, such as prior to the phase adjustment. FIG. 6 is copied from the article: https://www.semanticscholar.org/paper/Theta % E2%80%93gamma-coupling-in-the entorhinal % E2%80%93hippocampal-Colgin/ 4d21566e35Off22f4c03628f5dcaf50fa91430b0. Also with EEG, one can also measure the "surrogate/indirect" effect of phase coupling just from the sensor electrodes. In EEG, we can differ between "source space" and "sensor space". In source space, with enough electrodes, we can measure the phase in the hippocampal and near hippocampal regions (source space), and in sensor space, using for example frontal or occipital electrodes, we can measure the indirect effects of deep brain phase locking. So, preferably, hippocampus measurements within the source space are used to detect the theta-gamma coupling, but, instead, the coupling can be detected by using the sensor space.

Figure 2:
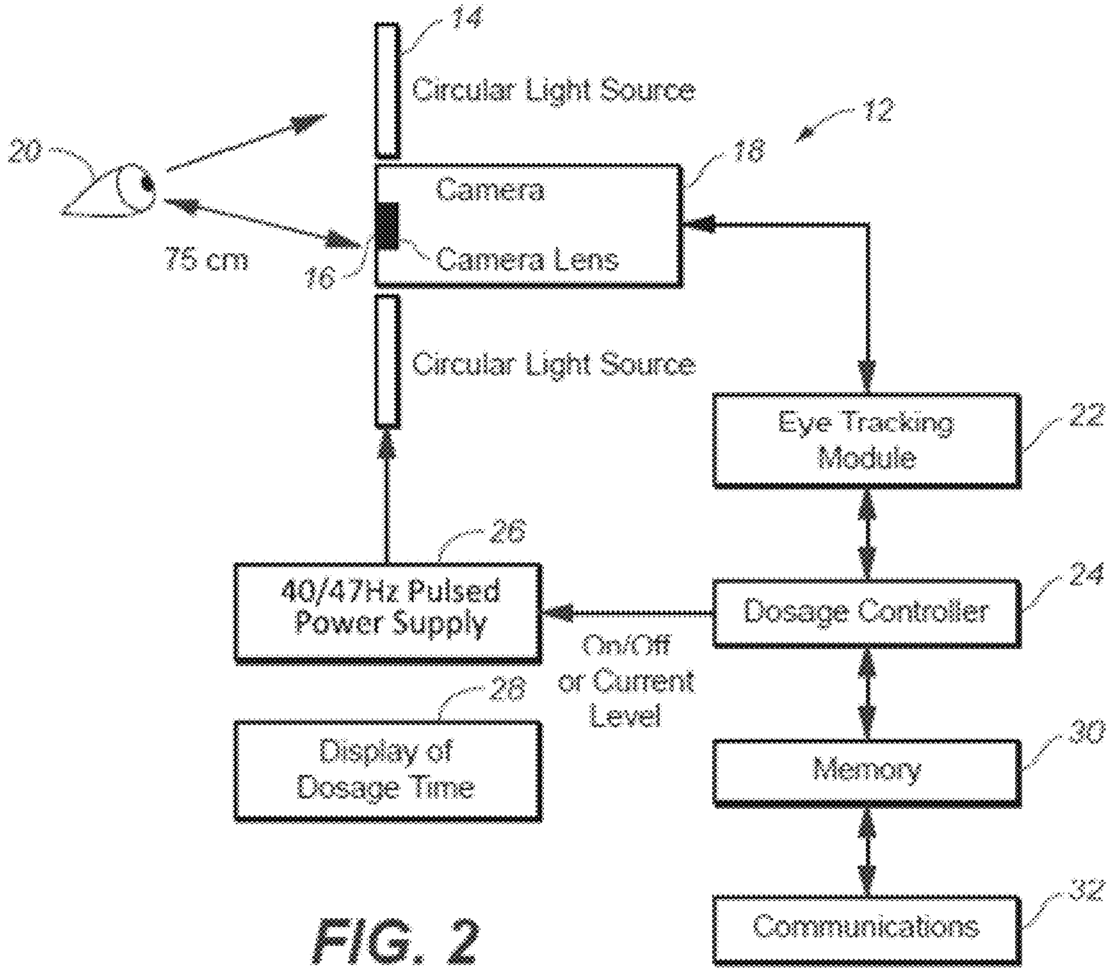
FIG. 2 illustrates various modules in the system.
Figure 3:
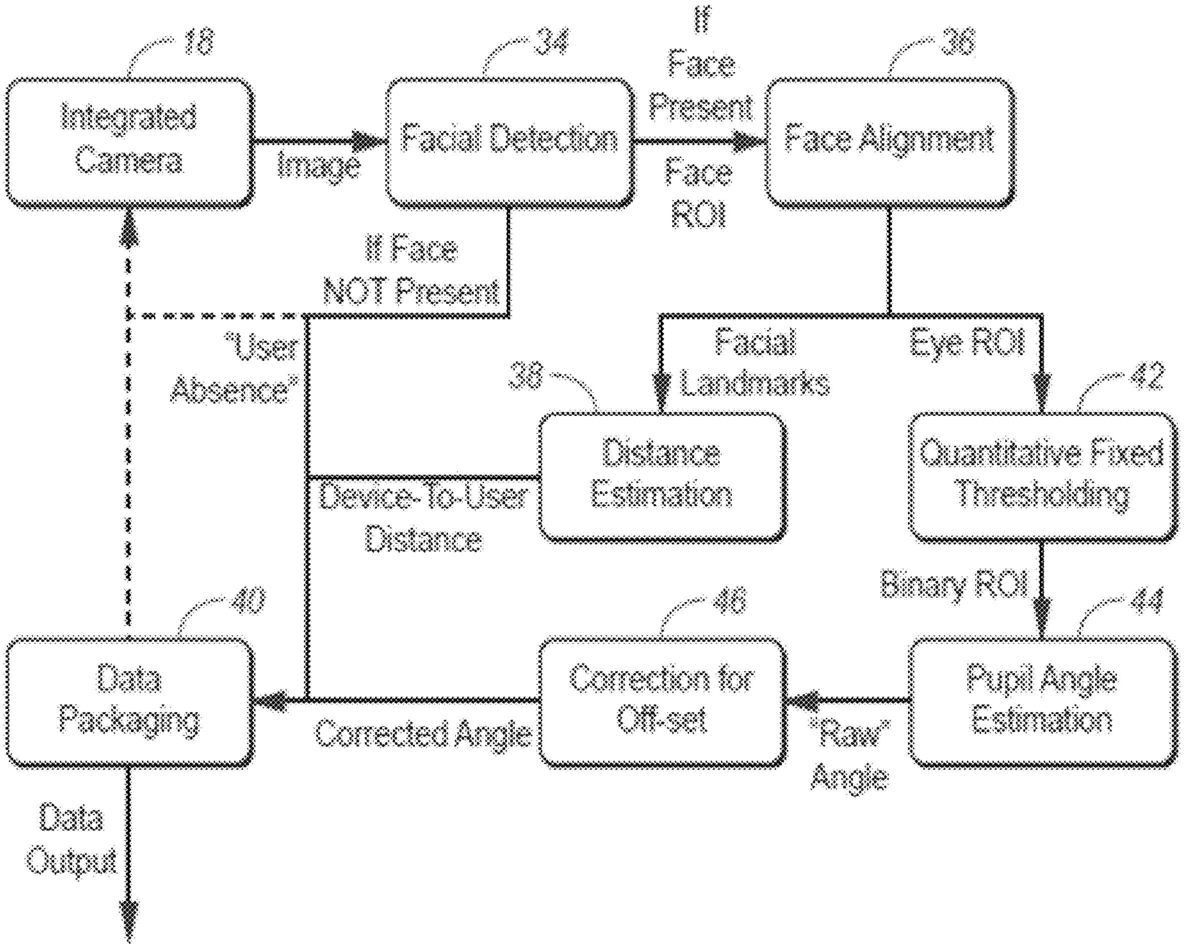
FIG. 3 illustrates the optical detection aspect of the system in more detail.
Figure 4:
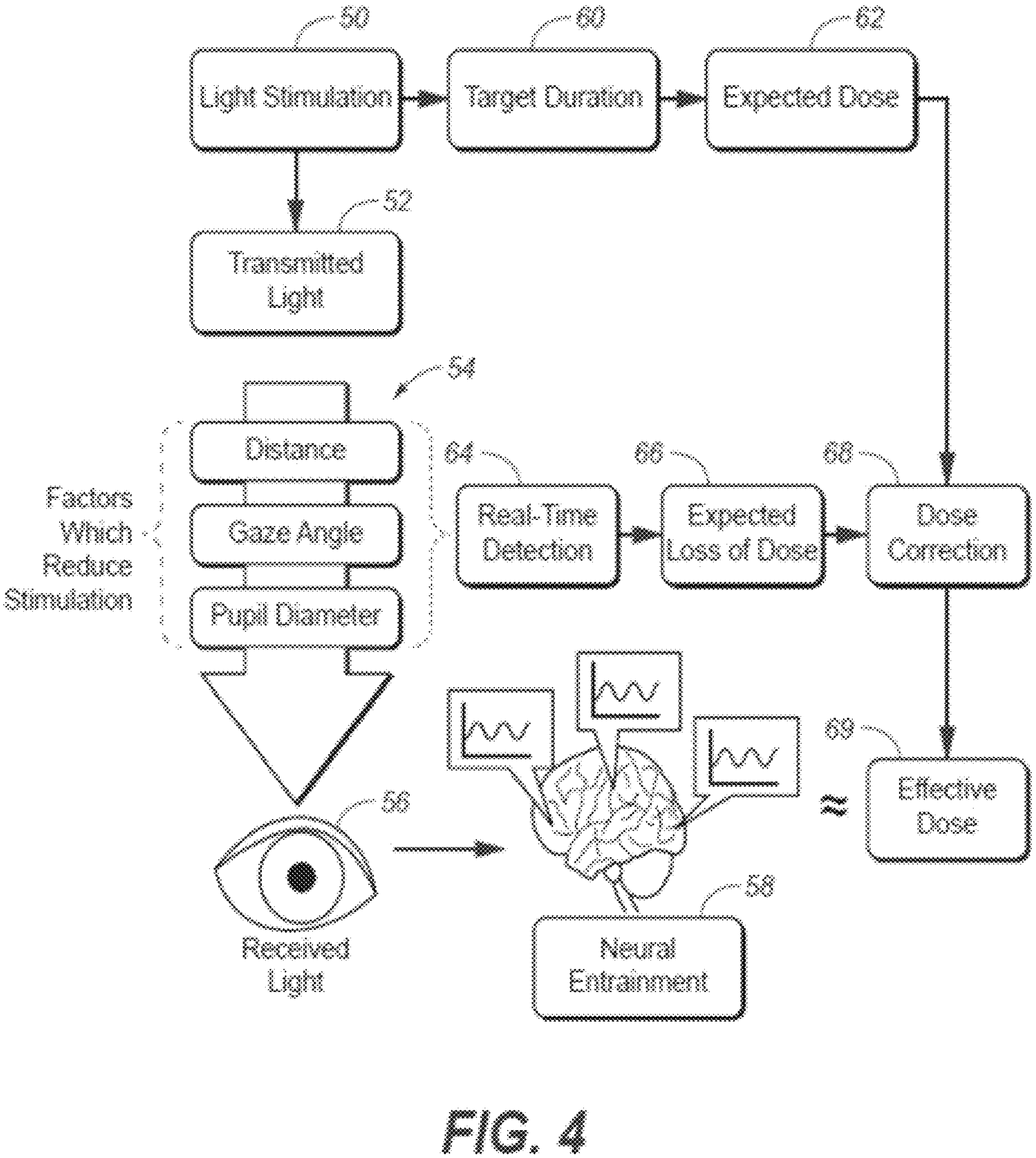
FIG. 4 is a flow chart illustrating the effect of various factors on gamma/theta brain stimulation dosage.

FIGS. 2-4 relate to achieving a predetermined dosage of the light stimulation.

In FIG. 2, the person's eye 20 is assumed to be looking above the light source 14. The camera 18, using image frames or reflected IR light, determines the gaze angle, distance, and pupil size. Gaze detection is commonly used in conjunction with display screens to detect which icon on the screen is being viewed by the viewer, and then to select that icon automatically. Gaze detection is also used in the retail industry to determine where a potential customer is looking. Gaze angle detection, including distance detection, is also used in various other fields and such systems are commercially available and inexpensive.

Suitable gaze detection systems for customization are available from SR Research, Tobi AB, and other companies. A fully customized system can also be fabricated using a Raspberry Pi Camera Module v2 in conjunction with a Raspberry Pi 3 Model B+ single board computer. Much of the software is commercially available.

The raw digital data from the camera 18 is then processed by a processor running an algorithm in the eye tracking module 22. Such algorithms may consist of publicly available software customized for the present invention. For the present invention, the software uses the resulting information about gaze angle, distance, and pupil size to dynamically control the dosage so that the person 10 ultimately receives the target dosage, in particular when the person is a patient.

The output of the eye tracking module 22 is then used to adjust the dosage that is controlled by the dosage controller 24. The dosage controller 24 initially receives a target dosage from the medical worker, which may correlate to a one-hour session. This target session time is then automatically extended based on deviations from the ideal conditions of direct gaze, 50 cm 25 distance, and average pupil size.

FIG. 2 shows the dosage controller 24 controlling a 40 Hz current pulse power supply and a 47 Hz current power supply 26 to be on a certain amount of time. The dosage controller 24 may also control the current applied to the light source 14. This will result in the person's brain perceiving a 40 Hz pulsed light and a 7 Hz pulsed light due to the beat frequency (subtraction frequency). In one embodiment, both a 40 Hz power supply and a 47 Hz power supply their current to different sets of LED distributed within the light source 14.

In another embodiment, the current supplied to the light source 14 is sinusoidal, and the energizing current is a gamma frequency and the gamma frequency plus a theta frequency.

The required session time is displayed to the person 10 on a display screen 28, so the person 10 knows that the session time has been extended due to the person 10 gazing away or being further than 50 cm from the light source 14. The display screen 28 may use data generated by the local system or generated by a remote system communicating via the Internet.

A memory 30 stores the results of the session so the medical worker has accurate data regarding the dosage. Communications hardware 32 may convey the data to the medical worker and update the system with upcoming session information.

FIG. 3 illustrates more detail about one embodiment of a suitable camera and algorithms. The algorithms and processor would be within the eye tracking module 22 of FIG. 2. The camera 18 captures an image of the person's face and eye position and analyzes the image. In other systems, IR is reflected off the person and the reflected light is processed. It is assumed that the system has undergone an initial calibration by the person.

In FIG. 3, the face is detected (block 34), such as using a Viola-Jones object detection algorithm. The face is the region of interest (ROI). If a face is detected, the ROI information is passed to a facial alignment block 36 that detects relative distances between facial features for distance estimation (block 38). The calculated distance is then provided in a data package (block 40).

The eyes are also detected and processed by quantitative fixed thresholding algorithms (block 42). This process uses contrast thresholds (binarization) to determine objects, such as irises and pupils. Based on this data, the pupil angle is estimated (block 44). From this, the angle of gaze is computed trigonometrically and, after correcting for any off-set (block 46) of the integrated camera 18 lens relative to the light source, the resulting angle is passed to the data packaging block 40 before capturing the next frame. The dosage may be adjusted dynamically from frame to frame or may just be adjusted nearer the end of the session.

If no face is detected, a "user absence" signal is generated, and no power is applied to the light source. The packaged data is applied to the dosage controller 24 of FIG. 2, as previously described, to adjust the session duration.

FIG. 4 is a flowchart showing the steps for dynamically controlling the dosage.

In step 50, the 40 Hz/47 Hz strobing light source is turned on to emit the stimulating light 52. The gaze detection system detects the person's distance, gaze angle, and pupil diameter (step 54) as the person's eye receives the light (step 56). The brain then undergoes neural entrainment (step 58) (i.e., the capacity of the brain to naturally synchronize its brainwave frequencies with the rhythm of periodic external stimuli).

The target duration (step 60), provided by the medical worker or other source, is correlated with an expected or target dosage of the light (step 62). The real-time detection (step 64) during the analysis of step 54 is then correlated to any expected loss of dosage (step 66) due to gaze angle, etc. A look-up table may be used to correlate the data with the loss of dosage.

The dose correction step 68 then subtracts the loss of dose from the "ideal conditions" dose to derive the actual effective dose being received by the person. The effective dose information (step 69) is then used to extend the session, as needed, to achieve the target dose.

The data obtained from the session and from testing the person, such as in particular a patient, may be used to further the understanding of the effects of the gamma brain stimulation on, for example, Alzheimer's disease or other neurological or psychiatric disorder (i.e., brain network dysfunctions).

Figure 5:
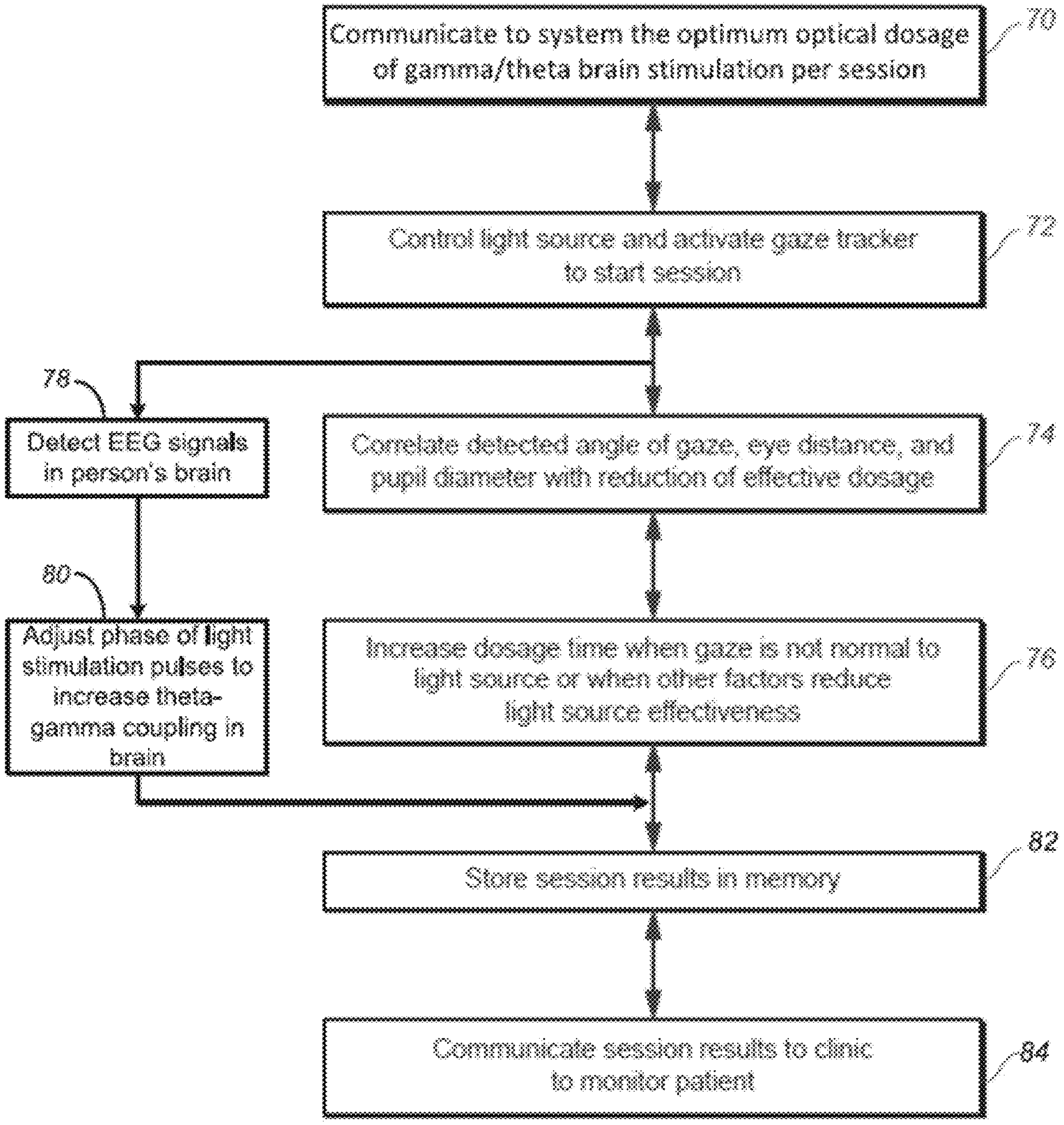
FIG. 5 is a flowchart identifying steps in a broad system process.

FIG. 5 is a broader flowchart summarizing certain steps in one method to achieve a desired dosage and also maximize theta-gamma coupling in the brain. In step 70, a medical worker or other source communicates to the system the optimal dosage of the gamma/theta brain stimulation, which may be in the form of a session duration time using a known light source.

In step 72, the light source and gaze tracker are activated to start the session.

In step 74, the detected gaze angle, eye distance, and pupil diameter are correlated with a reduction of the effective dosage.

In step 76, the session time is extended, as required, to compensate for the detected gaze angle, eye distance, and pupil diameter. In another embodiment, the target dosage presumes some variation from ideal of the detected gaze angle, eye distance, and pupil diameter, and the system can add or subtract from the session time.

In parallel with detecting the effective dosage, the phase of the light stimulation is controlled to maximize theta-gamma coupling in the brain. The system for adjusting the phase was described with respect to FIG. 1. In step78, the EEG signals from the MEC and CA1 areas of the brain are detected using sensors.

In step 80, the EEG signals are processed, and the phase of the light stimulation system is dynamically adjusted so that the two detected EEG signals have a high coupling, such as shown on the left side of FIG. 6.

In step 82, the session data is stored in a memory for evaluating the efficacy of the treatment.

In step 84, a communications system conveys the data to a clinic or other medical worker. The communications system can also receive information, such as the target dose.

The system may be used for therapy or just to analyze the effects of the optical gamma/theta brain stimulation on a group of similar persons for collecting further data for study. Other strobing frequencies besides 40 Hz and 47 Hz, as previously mentioned, may prove valuable with further studies.

The invention is not limited to a gamma/theta brain stimulation rate of 20-140 Hz and 4-10 Hz. Other frequency light pulses emitted by the light source 14 may be beneficial for beta brain waves (beta brain stimulation rate of 13-38 Hz) and circadian functions. By generating light greater than a frequency that causes perceptible flicker, and also generating light at that frequency plus a lower frequency, the original frequency and the subtraction frequency are perceived internal to the brain without the detection of flicker.

In another embodiment, the system is only used for gamma wave stimulation. For example, the first set of light sources may flicker at a frequency between 40 Hz and 60 Hz and the second set of light sources may flicker at a frequency between 74 Hz and 120 Hz.

In other embodiment, the optical system of FIG. 1 is combined with other systems that stimulate other senses, such as feel and hearing. The energizing of the LEDs in the light source 14 may also trigger electrical pulses to electrodes adhered to the person's skin to provide mild shocks, and/or the electrical signals may trigger sound pulses. Thus, different areas of the brain are simultaneously stimulated with the exact same gamma and theta waves. This skin and sound system is represented by the functional block 86 in FIG. 1.

The phases of the gamma and theta waves may also be varied for testing the results of different phases.

Figure 7A:
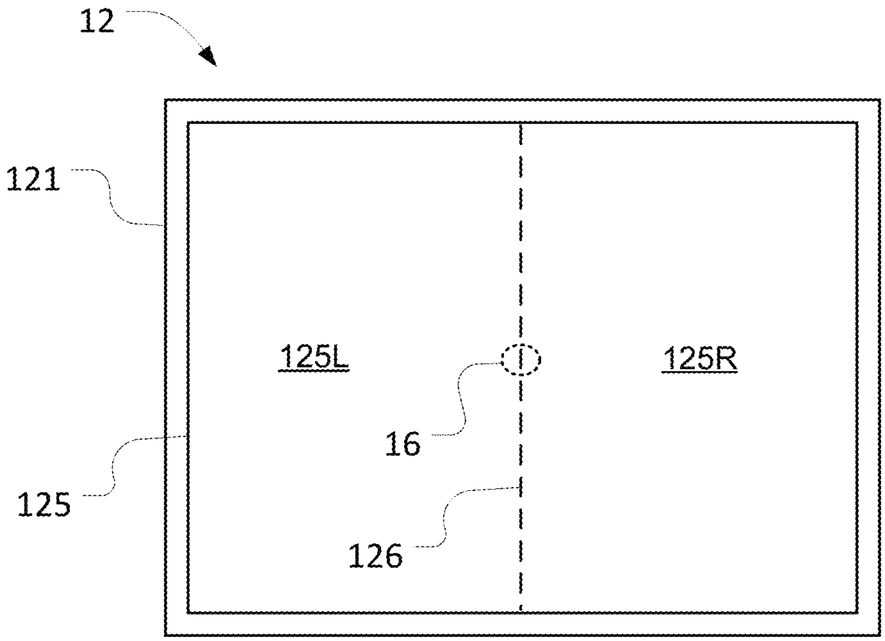
FIGS. 7A-B illustrate an embodiment of a phototherapeutic apparatus.
Figure 7B:
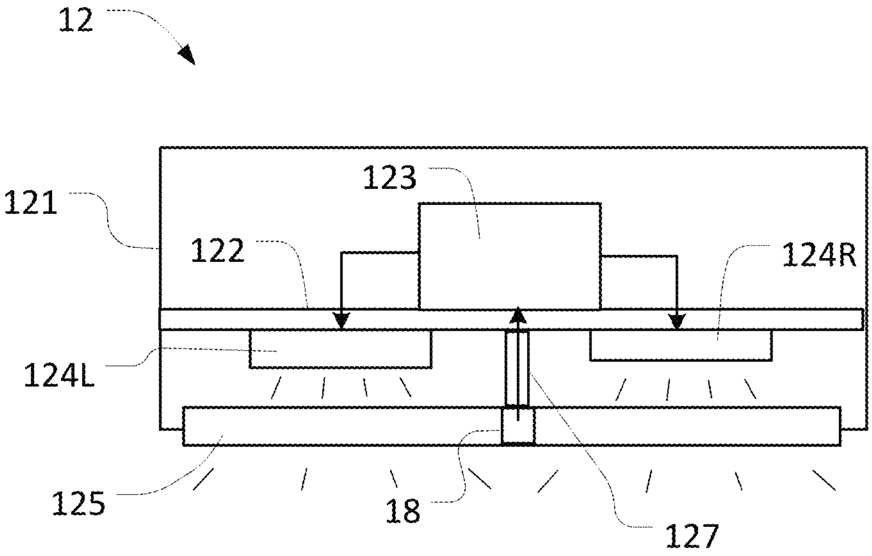

FIGS. 7A-B illustrate an embodiment of a phototherapeutic apparatus 12. FIG. 7A shows a schematic front view of the apparatus while FIG. 7B shows a schematic block diagram of the apparatus.

The phototherapeutic apparatus of this embodiment is implemented as a luminaire having a housing 121. The housing accommodates a light emitting member 125, a first set of light sources 124L, a second set of light sources 124R and a control circuit 123.

In the present example, the light sources 124L and 124R and the control circuit are mounted on a circuit board 122 or other suitable support member.

The first set of light sources 124L may comprise an array of one or more LEDs. Similarly, second set of light sources 124R may comprise an array of one or more LEDs. Each array of LEDs way include white LEDs or colored LEDs, such as LEDs of multiple different colors so as to be able to create heterochromatic flicker as described herein.

Operation of the two sets of light sources is controlled by the control circuit 123. To this end, the control circuit 123 may include a suitable power supply and a suitable driver circuit.

The light emitting member 125 is formed as a diffuser panel which may form part of the housing, e.g. it may form or be embedded in one side wall of the housing. The first set of light sources 124L are configured such that their light is emitted via one portion 125L, in this example, the left-side portion, of the light-emitting member 125. The second set of light sources 124R are configured such that their light is emitted via another portion 125R, in this example, the right-side portion, of the light-emitting member 125. The two portions 125L and 125R each form one half of the total light emitting surface of the light emitting member 125. Accordingly, when the sets of light sources are controlled to flicker at different frequencies, the two surface portions flicker at these different frequencies. In FIG. 7A, the border between the two portions 125L and 125R is schematically indicated by dashed line 126. It will be appreciated that, in some embodiments, the two portions may be separated by a visible border while, in other embodiments, there may be no visible border between the portions.

In the example of FIG. 7B, the apparatus includes a light barrier 127 configured to prevent light from the first set of light sources 124L to reach the second portion of the light emitting member 125R and to prevent light from the second set of light sources 124R to reach the first portion of the light emitting member 125L. In other embodiments, such a barrier may be omitted, e.g. because, in some embodiments, a certain amount of cross-over light may be acceptable or even desirable, and/or because one or more alternative means for directing the light from the sets of light sources to a selected portion of the light emitting member ae employed. For example, the light sources may include suitable lenses or other optical elements for selectively directing their light to the corresponding portion of the light emitting member.

The embodiment of FIGS. 7A and 7B further includes a camera 18 with lens 16 arranged centrally within the light emitting member. The camera is communicatively coupled to the control circuit and is used for e.g. gaze angle detection as described herein. In other embodiments, the camera may be positioned elsewhere, e.g. above or otherwise next to the light emitting member. In some embodiments, the camera may be omitted.

In the example of FIG. 7A, the light emitting member defines a generally rectangular light emitting surface. It will be appreciated that other embodiments may have a differently shaped light emitting surface, e.g. as illustrated in FIG. 8.

Figure 8:
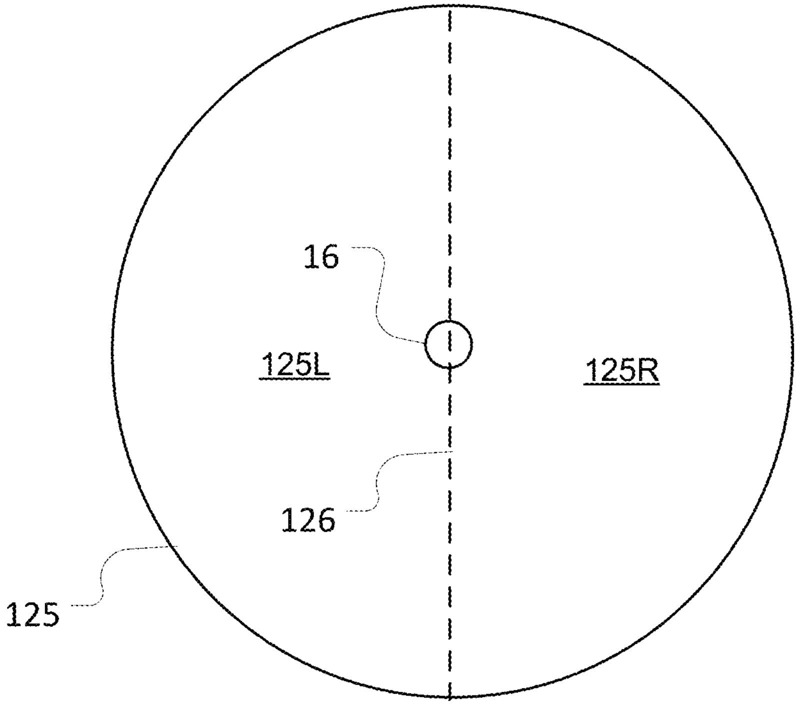
FIG. 8 illustrates an example of a light emitting surface of an embodiment of a phototherapeutic apparatus.

FIG. 8 illustrates another example of a light emitting surface 125 of an embodiment of a phototherapeutic apparatus. In the example of FIG. 8, the light emitting surface is circular or annular, optionally with a camera lens position in the center of the circle or ring-shaped light emitting member, e.g. as described in connection with FIG. 1. As in the previous embodiment, the light emitting surface is divided into a first portion 125L and a second portion 125R such that the first portion emits first light that varies at a first brain stimulation rate while the second first portion emits second light that varies at a second brain stimulation rate as described herein.

Figure 9:
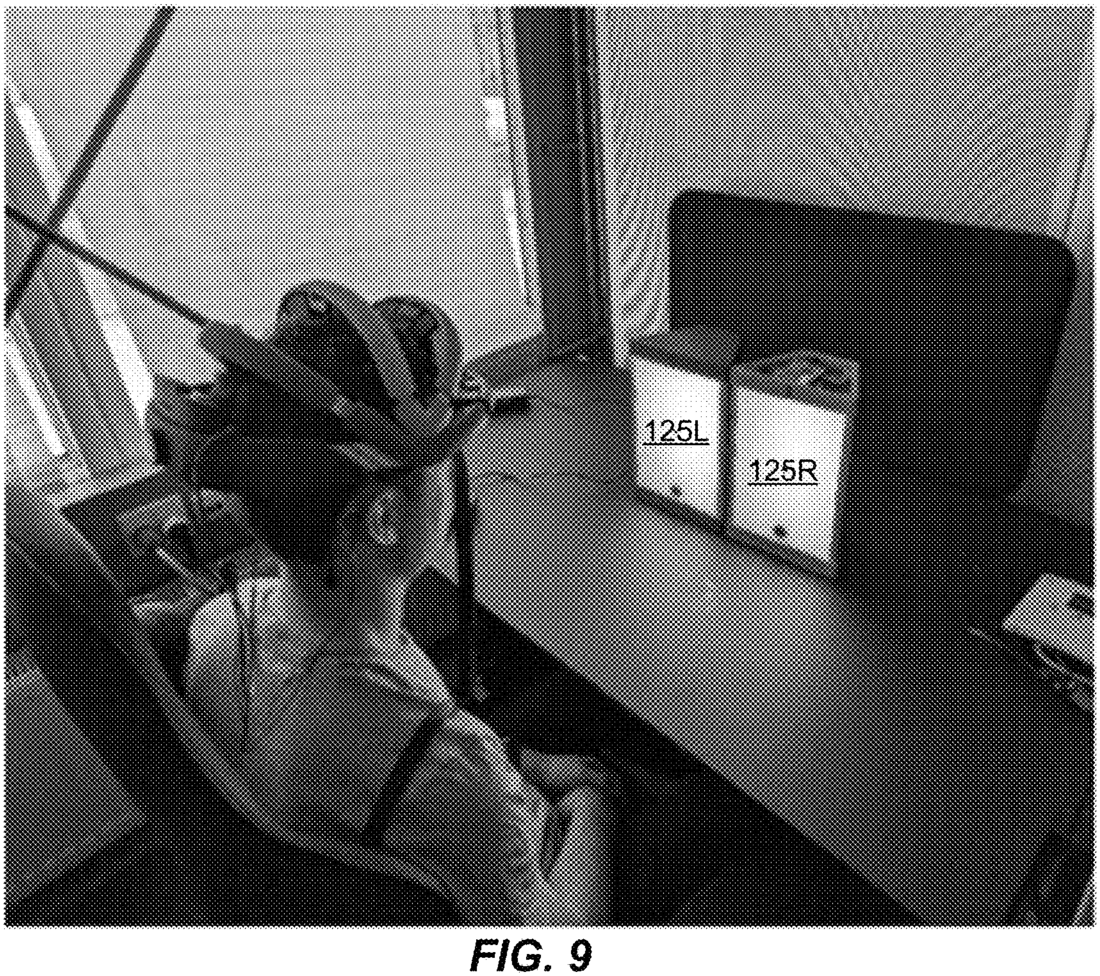
FIG. 9 shows an experimental setup with an embodiment of a phototherapeutic apparatus.

FIG. 9 shows an experimental setup with an embodiment of a phototherapeutic apparatus. In this example an phototherapeutic apparatus was used that has two housings, each accommodating a respective set of light sources and each defining a respective light emitting surface portion 125R and 125L, respectively. The light sources were controlled to flicker at respective brain stimulation rates. The flickering of each light source was a heterochromatic flicker, also referred to as Invisible Spectral Flicker (ISF). A subject was looking at the phototherapeutic apparatus while neural oscillations of the subject were recorded using an EEG sensor.

Figure 10:
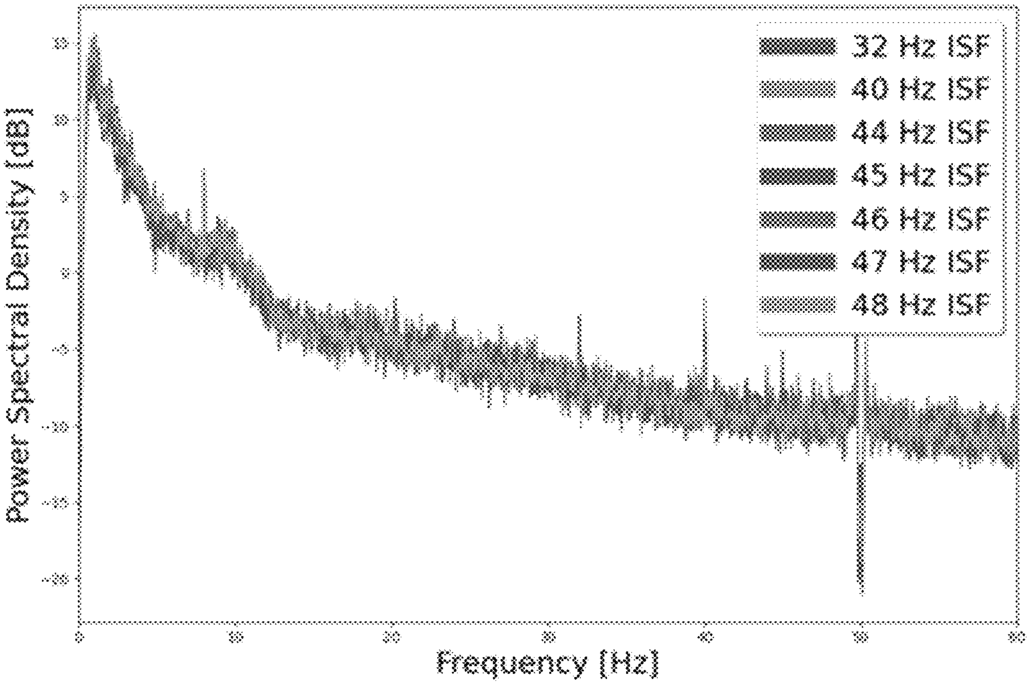
FIG. 10 shows recorded brain waves during use of an embodiment of a phototherapeutic apparatus.

FIG. 10 shows the power spectral density of recorded brain waves during use of an embodiment of a phototherapeutic apparatus. In particular, FIG. 10 shows the power spectral density of recorded brain waves during use of the apparatus shown in FIG. 9 operated to emit light flickering at 40 Hz via one light emitting surface portion 125L and light flickering at another brain stimulation rate via the other light emitting surface portion 125R. The flickering light emitted via both light emitting surface portions was ISF light as in Mikkel Pejstrup Agger et al., "Safety, Feasibility, and Potential Clinical Efficacy of 40 Hz Invisible Spectral Flicker versus Placebo in Patients with Mild-to-Moderate Alzheimer's Disease: A Randomized, Placebo-Controlled, Double-Blinded, Pilot Study", Journal of Alzheimer's Disease, 92(2), 653-665. https://doi.org/10.3233/JAD-221238. The experiment was repeated with respective values for the another brain stimulation rate, namely at 32 Hz, 40 Hz, 44 Hz, 45 Hz, 46 Hz, 47 Hz, and 48 Hz. The power spectral densities for the combination of 40 Hz flicker with each of the other brain stimulation rates are shown in FIG. 10. The combination of 40 Hz flicker and 40 Hz flicker thus serves as a comparative example where effectively only a single stimulation frequency of 40 Hz is applied. For the other experiments the difference frequency and thus the stimulated beat frequency varies.

As can be seen from FIG. 10, the recorded power spectral densities of all experiments show a strong peak at 40 Hz, as all experiments involved 40 Hz flicker via one of the light emitting portions. The power spectral densities also show peaks at the corresponding other brain stimulation rates. For example, the blue curve (combination of 40 Hz flicker and 32 Hz flicker) shows another peak at 32 Hz, while the red curve (combination of 40 Hz flicker and 45 Hz flicker) shows a peak at 45 Hz.

Yet further both combinations having a difference frequency of 8 Hz, i.e. the combination of 32 Hz and 40 Hz (blue line) and the combination of 40 Hz and 48 Hz (pink line) show a clear peak at 8 Hz confirming a considerable stimulation of neural oscillations at the beta frequency in the Theta range. Neural stimulation at the other beat frequencies was also present but at a lesser degree for this particular subject.

DEFINITIONS

The term "gamma/theta brain stimulation" means a stimulus, such as a light source, that can change the neuronal gamma and theta activity in the brain.

The term "person" means a subject to be subjected to gamma/theta brain stimulation, such as a patient exhibiting symptoms of a brain disease such as Alzheimer's, or such as a person who desires pre-emptive gamma/theta brain stimulation, or a test-person who is subjected to gamma/theta brain stimulation for instructive or test purposes. The term "stimulation session" means a procedure over time where the person is exposed to a brain-stimulating device to receive a certain dosage of light. A single stimulation session is typically conducted within a day, but a customized session can be expanded and individualized to comprise multiple days, weeks, or months.

The term "stimulation duration" means a time period of a stimulation session, but is not limited to comprising the whole session duration, since the stimulation session time period can be broken up into multiple individual durations allowing for "interval" training, such as 15 minutes×4=60-minute session. Strobing and flickering are used interchangeably in this application.

While particular embodiments of the present invention have been shown and described it will be obvious to those skilled in the art that changes and modifications may be made without departing from this invention in its broader aspects and, therefore, the appended claims are to encompass within their scope all such changes and modifications that are within the true spirit and scope of this invention.

The invention claimed is:

1. A phototherapeutic apparatus for emitting therapeutic light, the apparatus comprising:

a first set of one or more light sources and a second set of one or more light sources, the first set of the one or more light sources being different from the second set of the one or more light sources and being separately controllable;

a control module configured to control the first and second set of light sources, wherein the control circuit is configured to:

control the first set of light sources to generate first light, the first light varying periodically at a first brain stimulation rate;

control the second set of light sources, differently from the control of the first set of light sources, to generate second light concurrently with the first set of light sources generating the first light, the second light varying periodically at a second brain stimulation rate equal to the first brain stimulation rate plus a third brain stimulation rate, wherein the third brain stimulation rate is selected for stimulating neural oscillations at a beat frequency corresponding to said third brain stimulation rate.

2. The phototherapeutic apparatus according to claim 1, wherein the first brain stimulation rate is between 20 Hz and 140 Hz.

3. The phototherapeutic apparatus according to claim 2, wherein the first brain stimulation rate is between 20 Hz and 50 Hz.

4. The phototherapeutic apparatus according to claim 2, wherein the first brain stimulation rate is between 50 Hz and 140 Hz.

5. The phototherapeutic apparatus according to claim 4, wherein the first brain stimulation rate is higher than a critical flicker frequency (CFF) threshold, and wherein the control module is configured to control the first set of one or more light sources to emit light at a varying intensity, varying at the first brain stimulation brain rate.

6. The phototherapeutic apparatus according to claim 1, wherein a difference between the second brain stimulation rate and the first brain stimulation rate is between 1 Hz and 140 Hz.

7. The phototherapeutic apparatus according to claim 6, wherein the difference between the second brain stimulation rate and the first brain stimulation rate is between 1 Hz and 10 Hz.

8. The phototherapeutic apparatus according to claim 6, wherein the difference between the second brain stimulation rate and the first brain stimulation rate is between 20 Hz and 140 Hz.

9. The phototherapeutic apparatus according to claim 8, wherein the difference between the second brain stimulation rate and the first brain stimulation rate is substantially equal to the first brain stimulation rate.

10. The phototherapeutic apparatus according to claim 1, wherein the first brain stimulation rate is smaller than a critical flicker frequency (CFF) threshold; wherein the control module is configured to control the first set of light sources to alternatingly generate first and second colored light, alternatingly at said first brain stimulation rate, the first colored light having a first set of color components and the second colored light having a second set of color components different from the first set of color components; wherein the first and second color components are selected such that the alternatingly generated first and second colored light is perceivable by a human observer as light having a user-perceptible first fused color.

11. The phototherapeutic apparatus according to claim 1, wherein the second brain stimulation rate is smaller than a critical flicker frequency (CFF) threshold; wherein the control module is configured to control the second set of light sources to alternatingly generated third and fourth colored light, alternatingly at said second brain stimulation rate, the third colored light having a third set of color components and the fourth colored light having a fourth set of color components different from the third set of color components; wherein the third and fourth color components are selected such that the alternatingly generated third and fourth colored light is perceivable by a human observer as light having a user-perceptible second fused color.

12. The phototherapeutic apparatus according to claim 1, wherein one or both of the first and second generated light is white light.

13. The phototherapeutic apparatus according to claim 1, wherein the color and/or brightness of the first and/or second light is user-adjustable.

14. The phototherapeutic apparatus according to claim 1, wherein the first and second light have the same perceivable color and/or the same perceived brightness.

15. The phototherapeutic apparatus according to claim 1, comprising a housing configured to accommodate the first and second sets of light sources; the housing defining a light-output panel, in particular a diffuser panel, for outputting the first and second light towards a user; wherein the light-output panel defines a first panel portion and a second panel portion, different from the first panel portion; wherein the apparatus is configured to output the first light at least predominantly through the first panel portion and to output the second light at least predominantly through the second panel portion.

16. The phototherapeutic apparatus according to claim 15, wherein the light-output panel defines a light-output surface area, wherein each of the first and second panel portions have between 30% and 70% of the light-output surface area, such that the first and second panel portions together have between 80% and 100% of the light-output surface area.

17. The phototherapeutic apparatus according to claim 15, wherein the first and second panel portions are arranged next to each other in a side-by-side configuration.

18. The phototherapeutic apparatus according to claim 1, wherein the first set of light sources comprises a first set of light emitting diodes (LEDs), and wherein the second set of light sources comprises a second set of light emitting diodes (LEDs).

19. The phototherapeutic apparatus according to claim 1, further comprising:

one or more EEG sensors for detecting brain waves; and a processing system coupled to detect first signals corresponding to the brain waves and coupled to control one or more attributes of the generated light from the light source to increase one or more predetermined neural oscillation.

20. The phototherapeutic apparatus of claim 1, further comprising:

a processing system;

an eye-tracking device that detects said person's eye and provides first data to the processing system, wherein the processing system is configured to use the first data to adjust aspects of a brain stimulation session.

* * * * *